United States Patent
Flaven et al.

(10) Patent No.: US 9,192,487 B2
(45) Date of Patent: Nov. 24, 2015

(54) JOINT CONTROL SYSTEMS AND METHODS UTILIZING MUSCLE ACTIVATION SENSING

(71) Applicant: Arizona Board of Regents, a body corporate of the State of Arizona, acting for and on behalf of Arizona State University, Scottsdale, AZ (US)

(72) Inventors: Thierry Flaven, Saint Pierre d'Allevard (FR); Thomas G. Sugar, Tempe, AZ (US); George Wolf, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/202,771

(22) Filed: Mar. 10, 2014

(65) Prior Publication Data
US 2014/0257521 A1   Sep. 11, 2014

Related U.S. Application Data

(60) Provisional application No. 61/775,888, filed on Mar. 11, 2013.

(51) Int. Cl.
*A61F 2/72* (2006.01)
*A61F 2/66* (2006.01)
*A61F 2/68* (2006.01)
(Continued)

(52) U.S. Cl.
CPC .................. *A61F 2/72* (2013.01); *A61B 5/7203* (2013.01); *A61B 5/7207* (2013.01); *A61B 5/7214* (2013.01); *A61F 2/68* (2013.01); *A61F 2/76* (2013.01); *A61F 5/01* (2013.01); *A61B 5/6811* (2013.01); *A61F 2/6607* (2013.01); *A61F 2002/74* (2013.01); *A61F 2002/7615* (2013.01); *A61F 2002/7635* (2013.01)

(58) Field of Classification Search
CPC ........... A61F 2/68; A61F 2/72; A61F 2/6607; A61F 2/70; A61F 2/76; A61F 2/78; A61F 2/80; A61F 2002/6872; A61F 2002/7635; A61B 5/04888; A61B 5/6811; A61B 5/6812; A61B 5/72; A61B 5/7203; A61B 5/721; A61B 5/7214
USPC ...................................... 623/24, 25
See application file for complete search history.

(56) References Cited

U.S. PATENT DOCUMENTS 5,159,159 A * 10/1992 Asher ......................... 178/18.05
5,451,924 A *  9/1995 Massimino et al. ....... 340/407.1
(Continued)

OTHER PUBLICATIONS

Theisson. National Geographic. Bionics. Verified by the Wayback machine Oct. 5, 2011.*

(Continued)

*Primary Examiner* — Thomas J Sweet
*Assistant Examiner* — Christie Bahena
(74) *Attorney, Agent, or Firm* — Snell & Wilmer L.L.P.

(57) ABSTRACT

A system and method for controlling a prosthetic limb are provided. A sensor component receives input from a wearer's muscle and provides a signal to a control component. The sensor component may be a force sensing resistor placed inside a socket of a prosthetic limb between a residual limb and the hard side of the socket. The control component processes the signal and provides instructions to an actuation component. In this manner, an actuation component may move a joint, or may change the velocity of a joint, or may change other characteristics of the prosthetic limb.

10 Claims, 10 Drawing Sheets

(51) Int. Cl.
| | |
|---|---|
| A61F 2/76 | (2006.01) |
| A61B 5/00 | (2006.01) |
| A61B 5/01 | (2006.01) |
| A61F 5/01 | (2006.01) |
| A61F 2/74 | (2006.01) |

(56) References Cited

U.S. PATENT DOCUMENTS

| | | | | |
|---|---|---|---|---|
| 6,378,384 | B1* | 4/2002 | Atkinson et al. | 73/862.625 |
| 6,500,210 | B1 | 12/2002 | Sabolich et al. | |
| 7,137,998 | B2 | 11/2006 | Bedard | |
| 8,244,655 | B2 | 8/2012 | Hubbard et al. | |
| 8,551,029 | B1* | 10/2013 | Herr et al. | 602/16 |
| 2008/0046096 | A1 | 2/2008 | Bedard et al. | |
| 2009/0030530 | A1* | 1/2009 | Martin | 623/53 |
| 2009/0216156 | A1 | 8/2009 | Lengsfeld et al. | |
| 2012/0004736 | A1* | 1/2012 | Goldfarb et al. | 623/25 |
| 2012/0116256 | A1* | 5/2012 | Stavdahl et al. | 600/595 |
| 2012/0226197 | A1 | 9/2012 | Sanders et al. | |
| 2012/0330439 | A1 | 12/2012 | Goldfarb et al. | |
| 2013/0310979 | A1 | 11/2013 | Herr et al. | |

OTHER PUBLICATIONS

Blum. FSR-Controlled Prosthetic Hand. 2008.*
Buis, AWP. Calibration problems encountered while monitoring stump/socket interface pressures with force sensing resistors: techniques adpoted to minimise inaccuracies. Prosthetic Orthotic International. 1997. vol. 21, No. 3 pp. 179-182.*
Neumann, Edward. Use of a load cell and force-moment analysis to examine transtibial prosthesis foot rollover kintetics for anterior-posterior alignment perturbations. Journal of prosthetics and orthotics. 2012, vol. 24, No. 4. pp. 160-174.*
Sigdur, Gisli Karlsson. User Control of Lower Limb Prostheses. Copyright 2010.*
Carroll, Kevin. Prosthetics and Patient Management. Copyright 2006. pp. 160-161, Touch pads.*
Saether, Marthe. Practical Artifact Cancellation for Myoelectric Prosthesis Control. Jun. 2008. Masters Thesis Norwegian University of Science and Technology.*
Stilson, Tim. Resistance to Voltage. Oct. 17, 1996.*
Blum, Jeremy (1, 2). Using Force Sensors to Effectively Control a Below-Elbow Intelligent Prosthetic Device. Blog 2008.*
Fronczyk A., "Volitional Control of a Powered Prosthetic Ankle", Arizona State University, Jun. 2012.
Holgate M.A., "Control of a Robotic Transtibial Prosthesis", Arizona State University, Dec. 2009.
Hollander K.W. "Design and Control of Wearable Robot Actuators", Arizona State University, Dec. 2005.
C. J. De Luca, Surface Electromyography: Detection and Recording, DelSys Incorporated, 2002.
Sorin Herle and Sergiu Man (2009). Processing Surface Electromyographical Signals for Myoelectric Control, Rehabilitation Engineering, Tan Yen Kheng (Ed.), pp. 223-244.
Pons JL et al. "The MANUS-Hand Dextrous Robotics Upper Limb Prosthesis: Mechancial and Manipulation Aspects", Autonomous Robots 16, 143-163, 2004.
Micera S et al., "Hybrid Bionic Systems for the Replacement of Hand Function", Proceedings of the IEEE I vol. 94, No. 9, pp. 1752-1762, Sep. 2006.

Tura A et al., "Experimental development of a sensory control system for an upper limb myoelectric prosthesis with cosmetic covering", Yournal of Rehabilitation Research and Development vol. 35 No. 1, Jan. 1998 pp. 14-26.
Kiguchi K et al., "Development of a 3DOF mobile exoskeleton robot for human upper-limb motion assist", Robotics and Autonomous Systems 56 (2008) 678-691.
Ferris DP et al. "An improved powered ankle—foot orthosis using proportional myoelectric control", Gait & Posture 23 (2006) 425-428.
Huang H et al., "A Strategy for Identifying Locomotion Modes Using Surface Electromyography", EEEE Trans Biomed Eng. Jan. 2009 ; 56(1).
Isakov E et al., "Trans-tibial amputee gait: time-distance parameters and EMG activity", Prosthetics and Orthotics International, 2000, 24, 216-220.
Peeraer L et al., "DeveloDment of EMG-based mode and intent recogn&ion algorithms for a computer-controlled above-knee prosthesis", . Biomed. Eng. 1990, vol. 12, May, pp. 178-182.
Myers DR et al., "MyoelectricPatternRecognitionforUse in theVolitionalControlof Above-Knee Prostheses", IEEE Transactions on Systems, Man, and Cybernetics, vol. SMC-11,No. 4,Apr. 1981, pp. 296-302.
Au SK et al., "An EMG-position controlled system for an active ankle-foot prosthesis: An initial experimental study", Proceedings of the 2005 IEEE 9th International Conference on Rehabilitation Robotics Jun. 28-Jul. 1, 2005, Chicago, IL, USA.
Winter DA et al., "Biomechanics of Below-Knee Amputee Gait", J, Biomechanics, vol. 21, No. 5.pp. 361-367, 1988.
He J et al., "Engineering Neural Interfaces for Rehabilitation of Lower Limb Function in Spinal Cord Injured", Proceedings of the IEEE I vol. 96, No. 7, Jul. 2008, pp. 1152-1166.
Kobetic R et al., "Development of hybrid orthosis for standing, walking, and stair climbing after spinal cord injury", J. Rehabilitation Reseach and Development, vol. 46, No. 3, pp. 447-462, 2009.
Dillon GS et al., "Direct Neural Sensory Feedback and Control of a Prosthetic Arm", IEEE Transactions on Neural Systems and Rehabilitation Engineering, vol. 13, No. 4, pp. 468-472, 2005.
Zhou P et al., "Decoding a New Neural-Machine Interface for Control of Artificial Limbs", J Neurophysiol 98: 2974-2982, 2007.
Zhou P et al., "Towards Improved Myoelectric Prosthesis Control: High Density Surface EMG Recording After Targeted Muscle Reinnervation", Proceedings of the 2005 IEEE Engineering in Medicine and Biology 27th Annual Conference Shanghai, China, Sep. 1-4, 2005.
Hargrove LJ et al., "Real-Time Myoelectric Control of Knee and Ankle Motions for Transfemoral Amputees", JAMA, vol. 305, No. 15, pp. 1542 0-1544, 2011.
Silva J et al., "A Self-Contained, Mechanomyography-Driven Externally Powered Prosthesis", Arch Phys Med Rehabil vol. 86, pp. 2066-2070, 2005.
Weir RF et al., "Implantable Myoelectric Sensors (IMES) for Upper-E:xtremityProsthesis Control—Preliminary Work", Proceedings of the 25' Annual International Conference of the IEEE EMBS Cancun, Mexico Sep. 17-21, 2003.
Yakimovich T et al., "Design and Evaluation of a Stance-Control Knee-Ankle-Foot Orthosis Knee Joint", IEEE Transactions on Neural Systems and Rehabilitation Engineering, vol. 14, No. 3,, pp. 361-369, 2006.
Ha KH et al., "Volitional Control of a Prosthetic Knee Using Surface Electromyography", IEEE Transactions on Biomedical Engineering, vol. 58, No. 1, pp. 144-151, 2011.

* cited by examiner

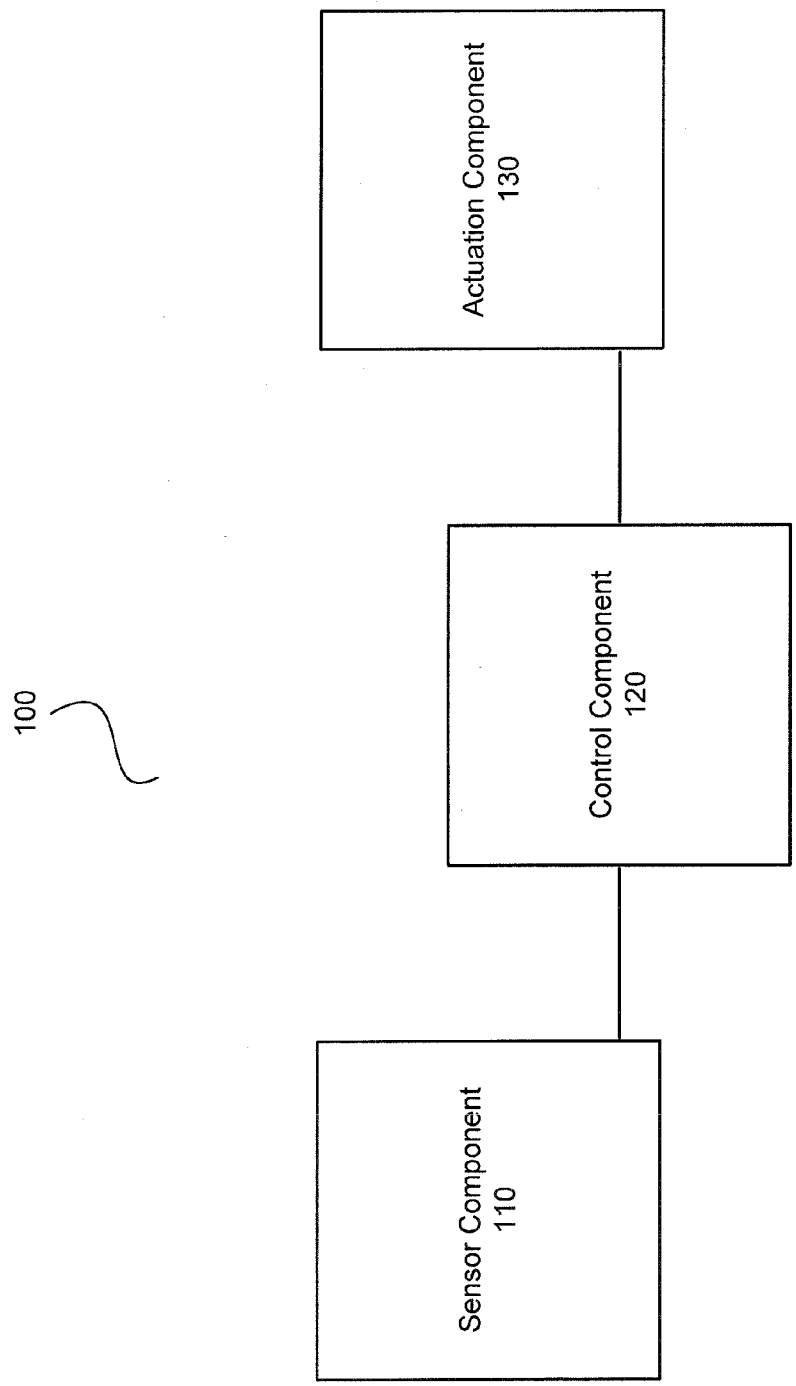

JOINT CONTROL SYSTEMS AND METHODS UTILIZING MUSCLE ACTIVATION SENSING

CROSS-REFERENCE TO RELATED APPLICATION

This application claims priority to, and the benefit of, U.S. Provisional Application Ser. No. 61/775,888 entitled "JOINT CONTROL SYSTEMS AND METHODS UTILIZING MUSCLE ACTIVATION SENSING" and filed Mar. 11, 2013, the contents of which are incorporated herein by reference.

TECHNICAL FIELD

The present disclosure relates to prosthetics, and in particular to sensing muscle activation in a residual limb to control a prosthetic device.

BACKGROUND

Controllable prosthetic devices for replacement of amputated or damaged limbs, such as hands, arms, legs, feet, and/or the like, have long been desirable, for example in order to improve quality of life for amputees. However, based at least in part on the amount of body tissue that is no longer present, control of such devices has often been rudimentary and/or poorly aligned to natural human movement.

For example, prior approaches for prosthetic ankle control have placed pressure sensors and force sensing resistors on the prosthetic foot to measure ground reaction forces. However, because of the number of steps and repeated kinetic shock, the force sensing resistors are not able to withstand the forces at the foot; they tend to break or the signal drifts over time.

Additionally, prior approaches have included using electromyography (EMG) and fine wire EMG sensors inside a prosthetic socket to determine muscle activation. However, the socket is often wet from perspiration, and the residual limb typically "pistons" up and down in the socket, so EMG sensor placement has been difficult and the resulting EMG readings are highly variable, making them poorly suited for use in prosthetic control. Accordingly, improved systems and methods for prosthetic control remain desirable.

SUMMARY

In various embodiments, a prosthetic control system is disclosed. A prosthetic control system may have a sensor component, a control component, and an actuation component. The sensor component may receive an input from the wearer of a prosthetic device and transmit a signal to a control component. The control component may process the signal received from the sensor component, and the actuation component may be coupled to the control component. The actuation component may modify a first characteristic of a prosthetic device in response to a first instruction received from the control component.

In various embodiments, a method of controlling a prosthetic device is disclosed. In various embodiments, the method may include receiving, by a sensor component, an input from the wearer of a prosthetic device. The sensor component may transmit a signal to a control component in response to the input. The control component may process the signal and determine a first instruction in response to the processing. Furthermore, the control component may transmit the first instruction to an actuation component. The actuation component may modify a first characteristic of a prosthetic device in response to the first instruction.

BRIEF DESCRIPTION OF THE DRAWINGS

With reference to the following description, appended claims, and accompanying drawings as attached:

FIG. 1 illustrates an exemplary prosthetic control system in accordance with various embodiments;

DETAILED DESCRIPTION

Figure 2A:
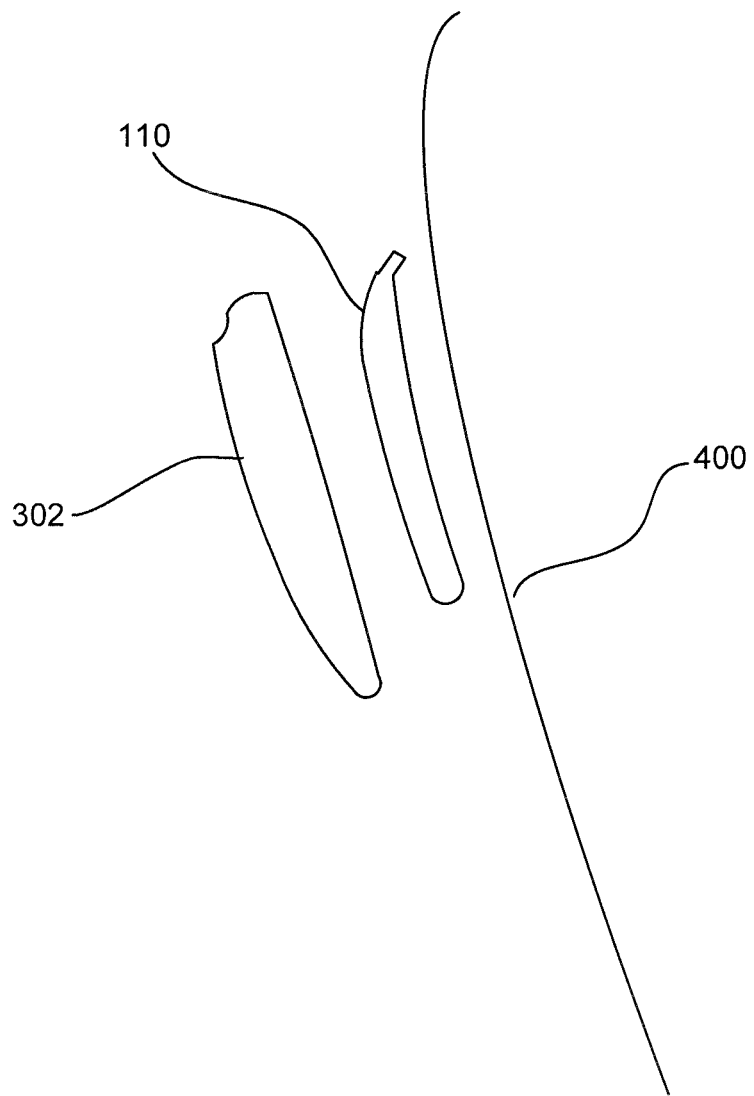
FIG. 2A illustrates exemplary sensor placement in an exemplary prosthetic control system in accordance with various embodiments.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of principles of the present disclosure.

For the sake of brevity, conventional techniques for pressure sensing, electronic control, biomechanical activation, and/or well-known physical and mathematical relationships may not be described in detail herein. Furthermore, the connecting lines shown in various figures contained herein are intended to represent exemplary functional relationships and/or physical or communicative couplings between various elements. It should be noted that many alternative or additional functional relationships or physical or communicative connections may be present in a practical prosthetic control system.

Prior approaches to prosthetic control have suffered from various deficiencies, for example poor calibration, inaccurate response, limited functional lifetime, and so forth. In contrast, exemplary prosthetic control systems configured in accordance with principles of the present disclosure provide reliable and accurate control of prosthetic devices, for example prosthetic ankle joints.

In accordance with principles of the present disclosure, a prosthetic control system may be any system configured to control a prosthetic device based at least in part on input from the wearer of the prosthetic device. In accordance with an exemplary embodiment, and with reference to FIG. 1, a prosthetic control system 100 generally comprises a sensor component 110, a control component 120, and an actuation component 130. Sensor component 110 is configured to receive an input from the wearer of a prosthetic device. Control component 120 is coupled to sensor component 110, and is configured to process signals received from sensor component 110. Actuation component 130 is coupled to control component 120, and is configured to activate, move, reposition, adjust, and/or otherwise modify a first characteristic of a prosthetic device, for example responsive to signals from control component 120. Moreover, a prosthetic control system 100 may be configured with any appropriate components and/or elements configured to provide control of a prosthetic device.

For example, in various embodiments, a prosthetic may comprise a first prosthetic member, a second prosthetic member, and a prosthetic control system arranged to control a first characteristic of the prosthetic. In various embodiments, this first characteristic comprises the movement of the second prosthetic member relative to the first prosthetic member. For example, with reference to FIGS. 2B and 2C, a prosthetic control system 100 may be positioned so that sensor component 110 and an actuation component 130 are disposed between first prosthetic member 302 and second prosthetic member 304. In this manner, prosthetic control system 100 controls the movement of second prosthetic member 304 relative to first prosthetic member 302. In various embodiments, first prosthetic member 302 comprises a socket into which a residual limb may be inserted, and second prosthetic member 304 comprises a jointed component, for example, an artificial foot, mechanically connected to the socket by an articulating joint and/or brace.

With reference again to FIG. 1, in various embodiments, sensor component 110 may comprise any suitable pressure sensor, for example a force-sensing resistor (FSR). Moreover, sensor component 110 may comprise a strain gauge, a piezoelectric and/or piezoresistive sensor, a capacitive sensor, an optical sensor, and/or the like. In various embodiments, more than one sensor component 110 is incorporated. By implementing more than one sensor component 110, pressure from a variety of locations may be sensed, for example, to permit more degrees of control, to permit more precise control, and/or to aid in filtering out noise, for example common-mode noise.

In various exemplary embodiments, sensor component 110 is affixed to and/or coupled to a portion of a prosthetic. For example, with reference to FIGS. 2B and 2C, in various embodiments, a sensor component 110 is disposed inside a first prosthetic member 302. In various exemplary embodiments, a sensor component 110 is affixed to the socket of a prosthetic. In other exemplary embodiments, a sensor component 110 is installed in the socket liner. Moreover, a sensor component 110 may be disposed at any suitable location, for example a location configured to sense muscle activation of a residual limb. When a muscle of the residual limb is flexed, it pushes against sensor component 110, which is in turn pressed against the socket, and thus compressed. In this manner, the sensor component 110 may detect a force or pressure exerted by the muscle and/or otherwise detect activation of the muscle.

With additional reference to FIG. 2A, in an exemplary embodiment, a sensor component 110 may be affixed to the first prosthetic member 302. In various embodiments, the first prosthetic member 302 comprises a hard socket adapted to receive a residual limb comprising a muscle 400. When the muscle 400 is flexed, the muscle 400 pushes against the sensor component 110. The amount of pressure detected by a sensor component 110 may be utilized by control component 120 (see FIG. 1), for example to determine a position, velocity, or force for a component of a prosthetic, for example an ankle joint 132 (see FIG. 2B) and/or a brace 134 (see FIG. 2C) and/or a second prosthetic member 304 (see FIG. 6).

For example, with reference now to FIG. 2A wherein a detailed view of an exemplary sensor placement is illustrated, in various embodiments a sensor component 110 is located in a position wherein the pressure exerted by a muscle 400 on the sensor component 110 is adequately reacted by the first prosthetic member 302 so that sensor component 110 does not move and/or is not dislocated relative to first prosthetic member 302 when pressed. Additionally, the sensor component 110 may be located in a position wherein the axis of force exerted by the muscle 400 is approximately tangential and/or perpendicular to the shear/stress forces created when the socket contacts the residual limb while in use. For example, with reference to FIGS. 2B and 2C, the sensor may be located on the first prosthetic member 302 in a position substantially coplanar to a plane lying normal to the axis of ankle joint 132. Alternatively, the sensor component 110 may be located in any position arranged to diminish unwanted signal noise, for example noise caused by the residual limb contacting the socket.

Moreover, in various example embodiments, multiple sensor components 110 having four force sensing resistors may be implemented, for example, to capture and detect pressure variations as a determination of gait events. For example, it is expected that during level ground walking sensor pairs located at points anterior-proximal and posterior-distal in the sagittal plane would rise and fall together.

Figure 6:
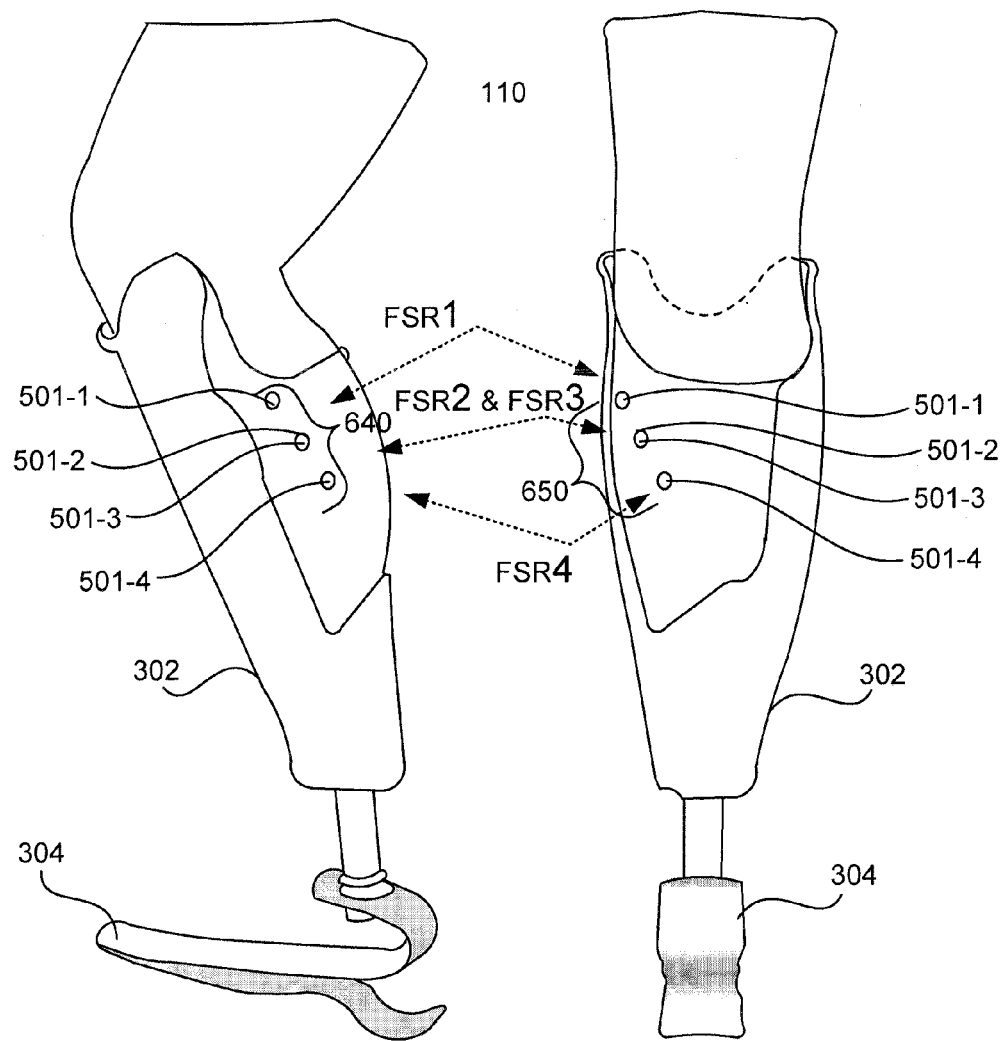
FIG. 6 illustrates exemplary sensor placement in an exemplary prosthetic control system for a below the knee prosthetic having a plurality of sensor components in accordance with various embodiments.

For example, with reference to FIG. 6, in various embodiments, four sensor components 110 may be implemented as a first sensor set 640 and four sensor components 110 may be implemented as a second sensor set 650. First sensor set 640 and second sensor set 650 may be positioned so that corresponding sensor pairs located at points anterior-proximal and posterior-distal in the sagittal plane rise and fall together.

Figure 8:
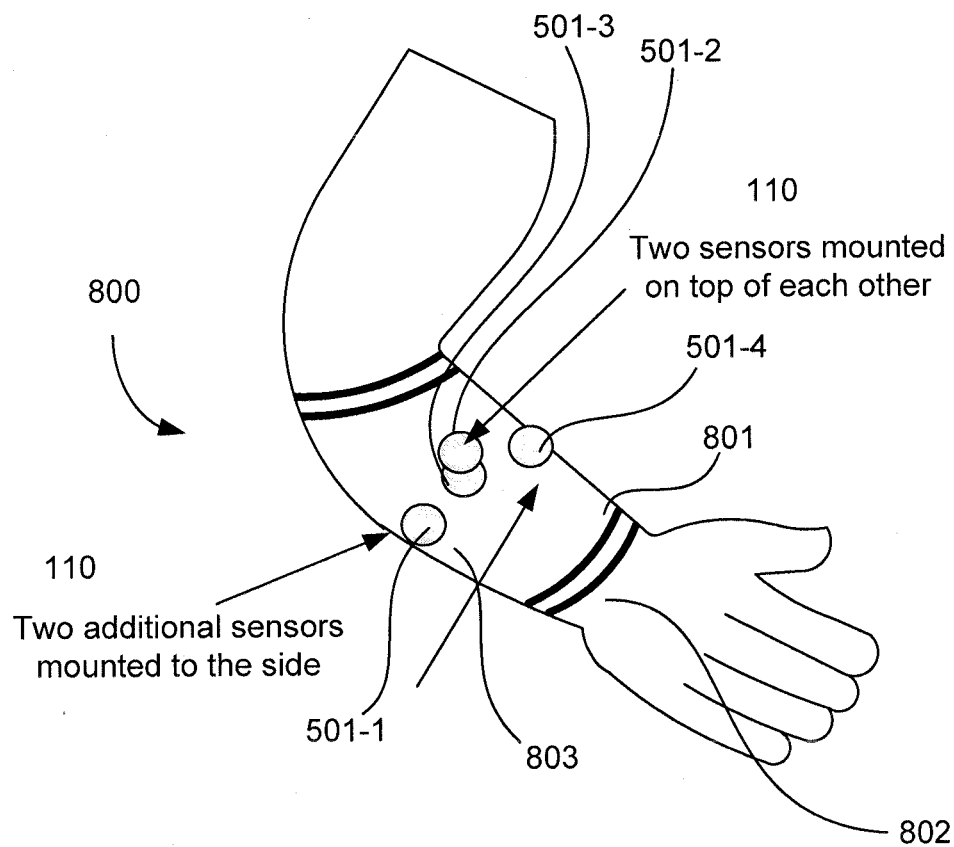
FIG. 8 illustrates exemplary sensor placement in an exemplary prosthetic control system having a control sleeve having four force sensing resistors in accordance with various embodiments.

With reference to FIG. 8, a sensor component 110 may be positioned in a control sleeve 800. While a sensor component may be mounted inside a portion of a prosthetic, as discussed elsewhere herein, in various embodiments, a sensor component may be mounted inside a separate control sleeve 800. In various embodiments a control sleeve 800 comprises a fabric sleeve 801, sensor component 110, and retention element 803. In various embodiments, fabric sleeve 801 wraps sensor component 110 and maintains sensor component 110 in contact with a portion of a body, for example forearm 802. Retention element 803 may comprise an elastic band or the like. Retention element 803 may be tightened around the sleeve, for example, so that a firm but comfortable bias force maintains sensor component 110 position. In this manner, the opening and closing of a wearer's hand may be detected by the sensing of muscle activation in the forearm 802. In accordance with the principles herein, sensor component 110 may be mounted in a control sleeve 800. For example, four sensor components 110 comprising force sensing resistors may be implemented in communication with a sensor component interface component 501 comprising a Wheatstone bridge.

Figure 2B:
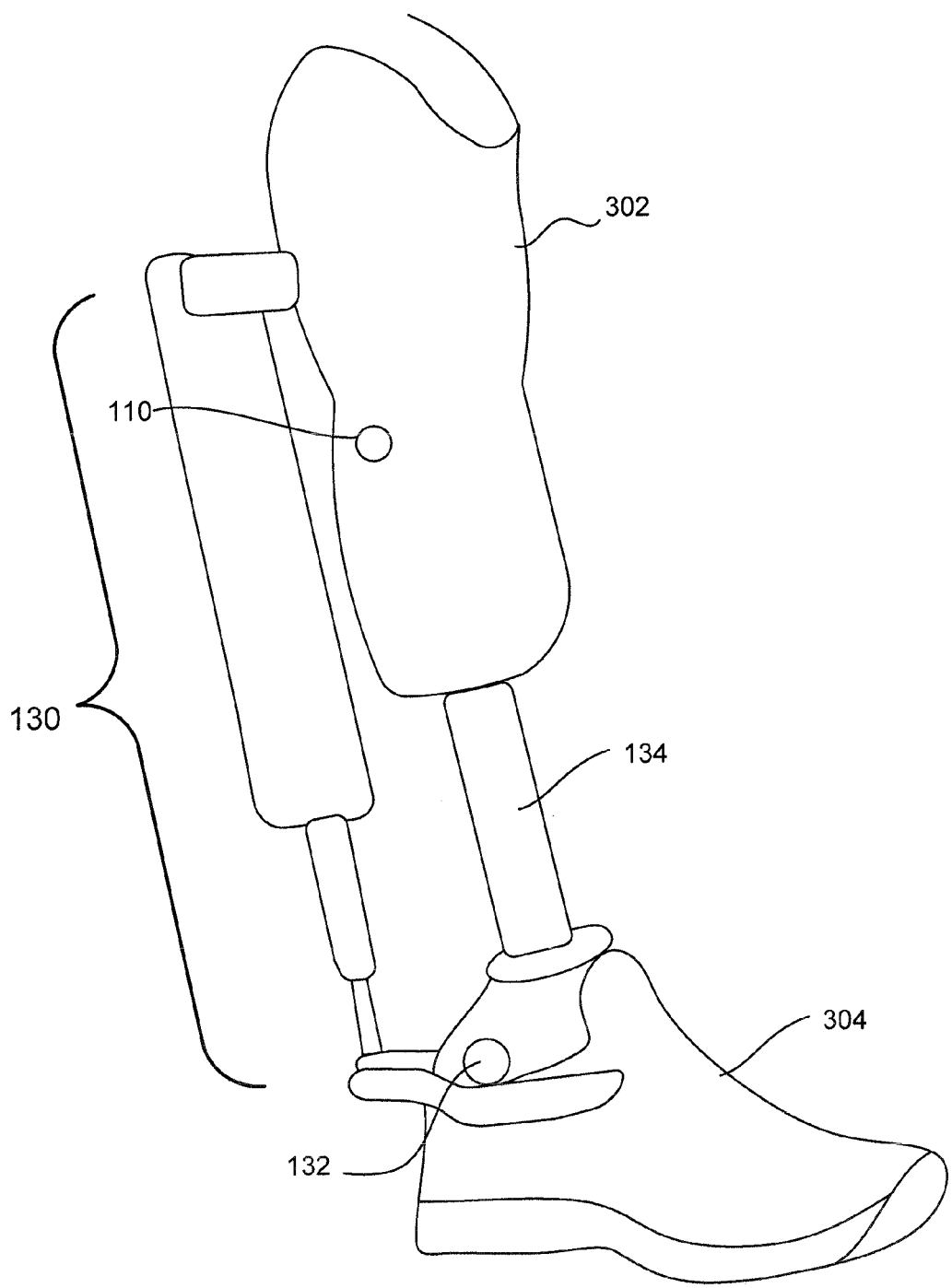
FIG. 2B illustrates use of an exemplary prosthetic control system in connection with control of a prosthetic ankle in accordance with various embodiments.
Figure 2C:
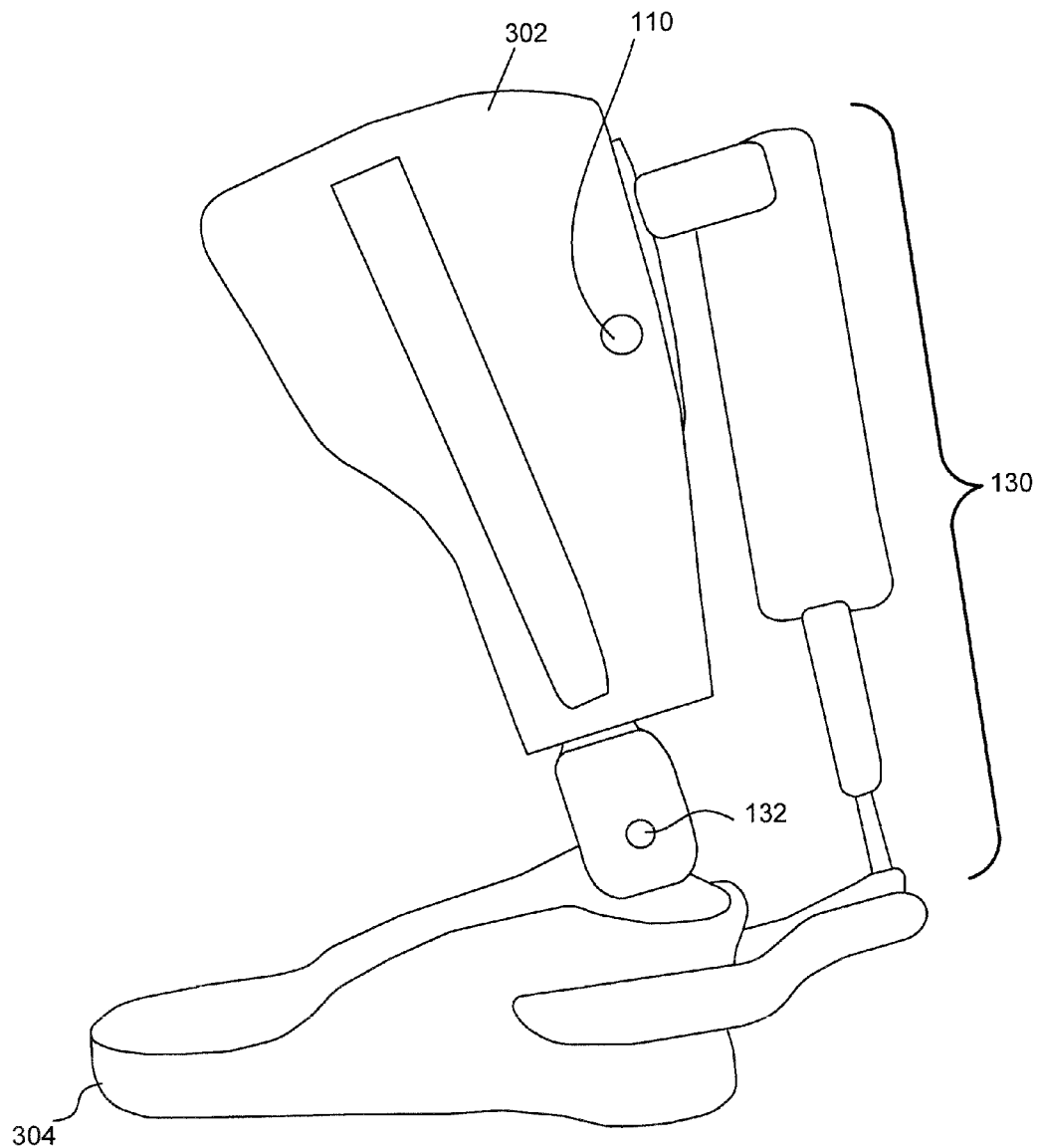
FIG. 2C illustrates use of an exemplary prosthetic control system in connection with control of a brace in accordance with various embodiments.

In accordance with principles of the present disclosure, in various embodiments, the sensor component 110 is located in the popliteal depression, for example behind the knee. In various embodiments, the sensor component 110 is located at the medial gastrocnemius. Moreover, the sensor component 110 may be located at the lateral gastrocnemius, for example as illustrated in FIGS. 2B and 2C. The sensor component 110 may be located at any location selected to permit a desired muscle to exert a desired pressure and having sufficiently minimal noise to permit reliable operation. With reference to FIG. 2A, in various embodiments, the force exerted on the sensor component 110 may be varied by the wearer in response to the wearer variably contracting the muscle 400.

With renewed reference to FIG. 1, in various exemplary embodiments control component 120 may comprise any suitable electronic components configured to provide control of a prosthetic device (or portion thereof) in response to a signal from sensor component 110, for example microprocessors, electronic memories, communications ports and associated protocols, and/or the like. In an exemplary embodiment, control component 120 comprises one or more of a force sensor interface component and one or more of a logical controller.

Figure 3:
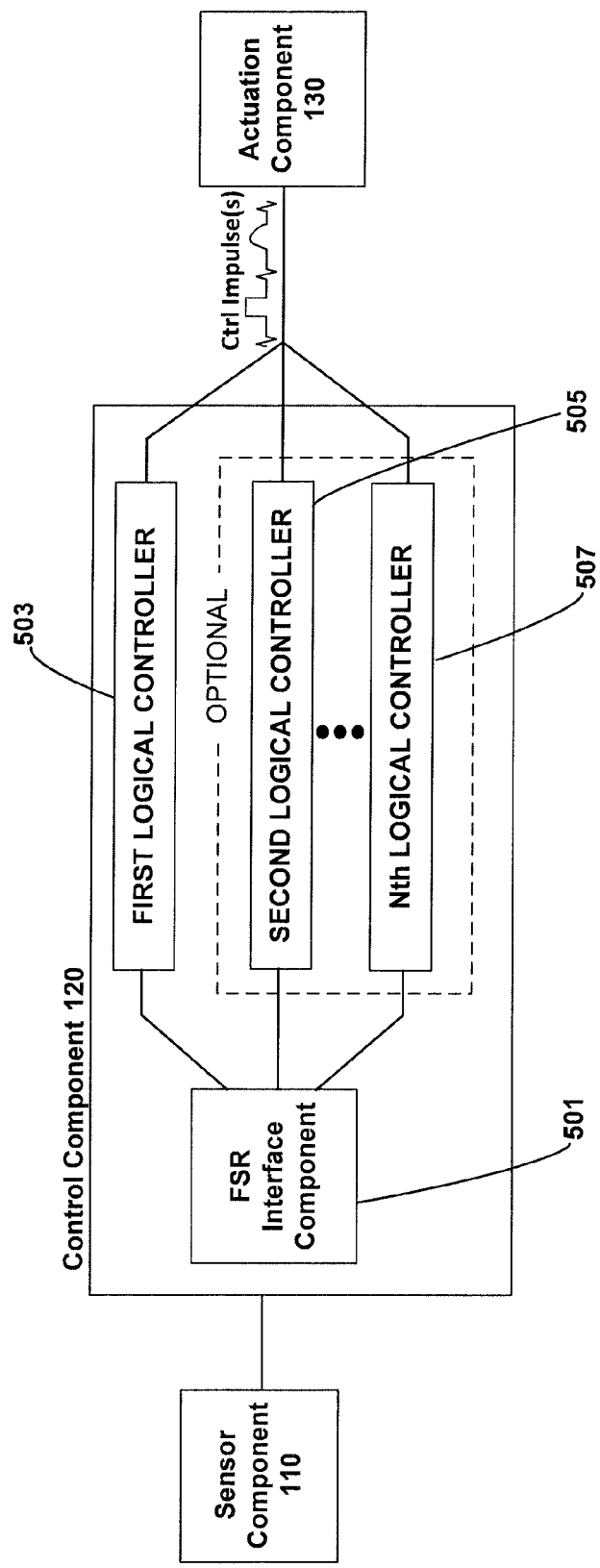
FIG. 3 illustrates various elements of an exemplary prosthetic control system, in accordance with various embodiments.

With reference now to FIGS. 1 and 3, in various embodiments control component 120 comprises a force sensor interface component 501. In various embodiments, a force sensor interface component 501 may comprise a voltage divider circuit, a Wheatstone bridge circuit, and/or the like. In various embodiments, a voltage divider circuit may be implemented. A voltage source may be divided across two resistors, and the divided voltage may be measured at the juncture of the resistors. For example, a force sensing resistor may be disposed between a voltage source and a first juncture. A fixed resistor may be disposed between the first juncture and a voltage sink. The divided voltage may be measured between the voltage sink and the juncture. In this manner, as the resistance of the force sensing resistor varies in response to the degree of pressure exerted on the force sensing resistor by the wearer's muscle, the divided voltage correspondingly varies, and such voltage may be utilized in connection with operation and/or control of prosthetic control system 100.

In other example embodiments, the force sensor interface component 501 may comprise a Wheatstone bridge. In this manner, common mode noise may be filtered, for example, by implementing multiple force sensing resistors in a Wheatstone bridge configuration. In various other embodiments, only one force sensing resistor is implemented. In certain embodiments, a Wheatstone bridge is implemented, for example to facilitate different interconnections between various aspects of a logical controller and a force sensor interface component.

Figure 4:
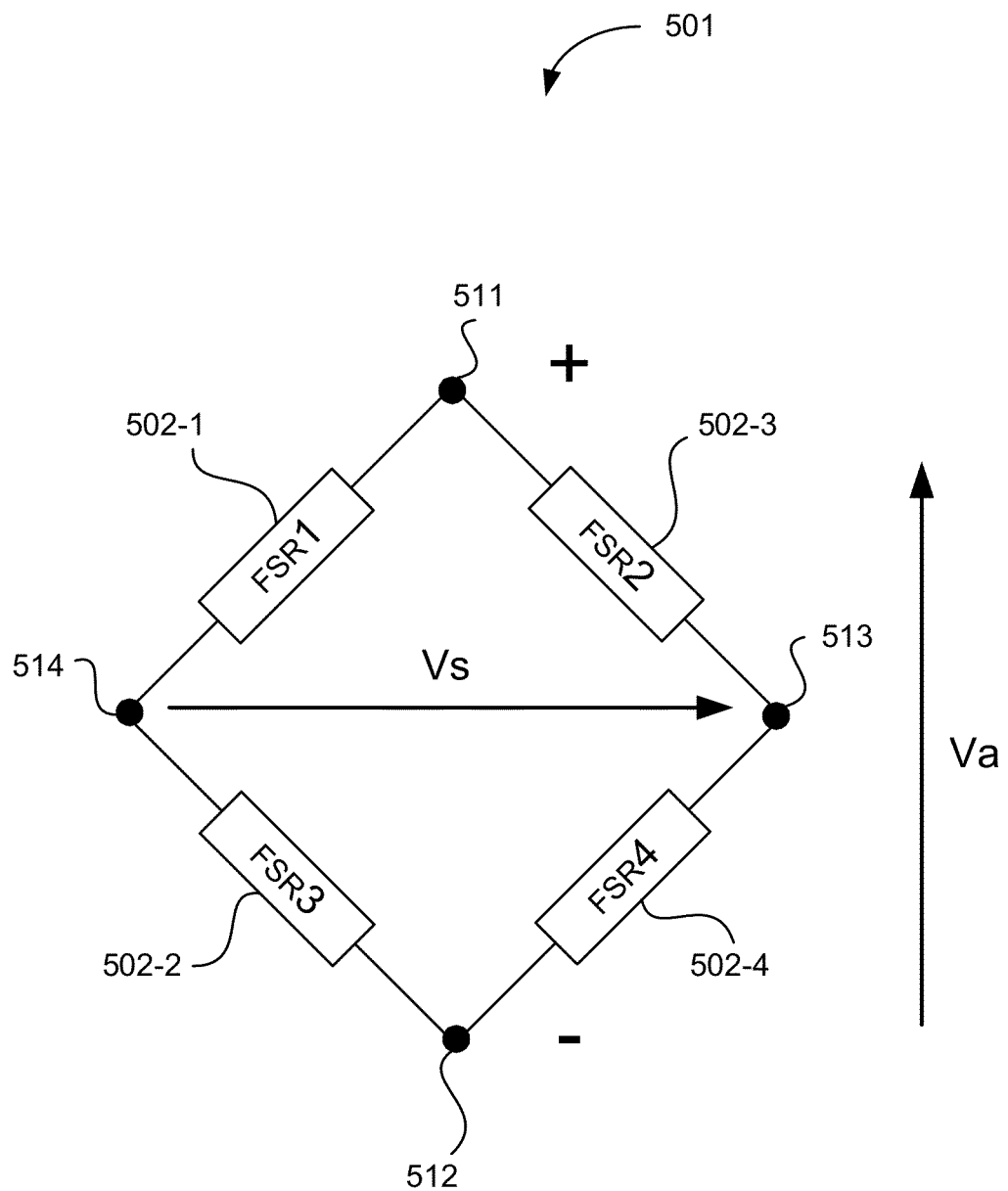
FIG. 4 illustrates various aspects of a prosthetic control system having four force sensing resistors in a Wheatstone bridge configuration in accordance with various embodiments.

For example, with reference to FIG. 4, in conjunction with at least one sensor component 110, a force sensor interface component 501 comprises a Wheatstone bridge circuit connecting four sensor components 110. A Wheatstone bridge may be used in sensor electronics to amplify small signals while rejecting common, extraneous signals such as temperature and or drift. In various embodiments, four resistors are arranged in two branches of two resistors connecting at the positive and negative voltage source. Four sensor components 110 may be connected with a force sensor interface component 501 comprising a Wheatstone bridge. For example, resistor 502-1, resistor 502-2, resistor 502-3, and resistor 502-4 may comprise force sensing resistors. In this regard, a constant voltage, Va, is applied to the circuit across positive input terminal 511 and negative input terminal 512. A sensed voltage, Vs, is measured across the bridge circuit output terminal 513 and negative output terminal 514.

Figure 5:
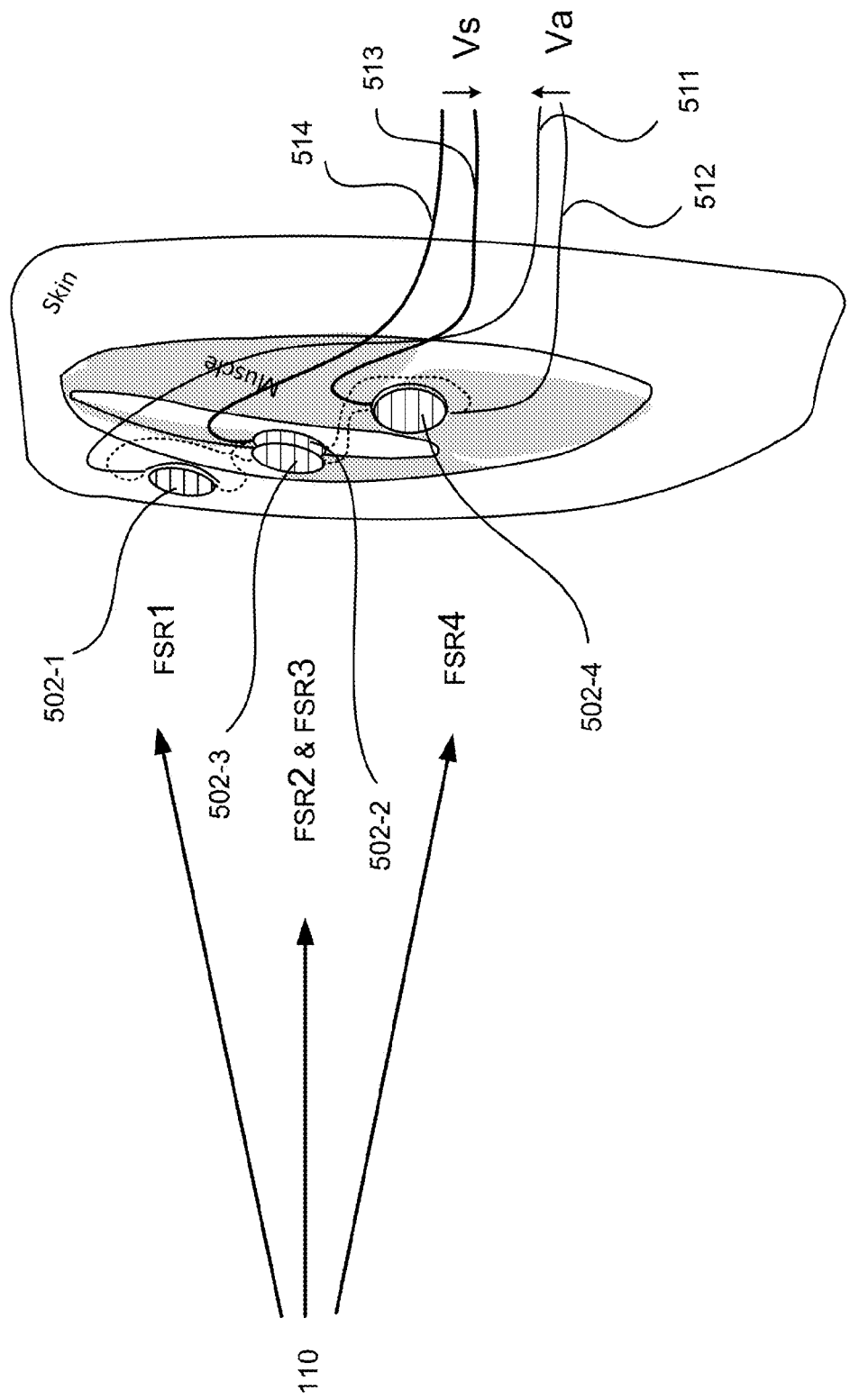
FIG. 5 illustrates exemplary sensor placement in an exemplary prosthetic control system having four force sensing resistors with two force sensing resistors placed on top of each other on the muscle belly and two force sensing resistors placed adjacent to the muscle belly, in accordance with various embodiments.

In various example embodiments, four sensor components 110 comprising force sensing resistors are arranged in a single Wheatstone bridge shown in FIGS. 4, 5, 6, and 8. The sensors are arranged so that resistor 502-2 and resistor 502-3 are on top of each other and, ideally, measure substantially the same force. The force from the socket pressure plus the muscle activation force are measured by resistor 502-2 and resistor 502-3 while resistor 502-1 and resistor 502-4 measure the same residual level of pressure or force inside the socket. As shown in FIGS. 5, 6, and 8, resistor 502-2 and resistor 502-3 are placed on the muscle belly while resistor 502-1 and resistor 502-4 are placed to the side of the muscle belly. When the pressure or force measured by resistor 502-1 equals resistor 502-4, and the pressure or force measured by resistor 502-2 equals resistor 502-3, the circuit gain equation simplifies to:

$$\frac{V_s}{V_a} = \frac{(R_{FSR1} - R_{FSR3})}{(R_{FSR1} + R_{FSR3})}$$

where $R_{FSR1}$ is resistor 502-1, $R_{FSR2}$ is resistor 502-2, $R_{FSR3}$ is resistor 502-3, and $R_{FSR4}$ is resistor 502-4.

The voltage sensed is directly proportional to the difference in resistance, R, of resistor 502-1 and resistor 502-3. The denominator is the sum of the resistance, R, of resistor 502-1 and resistor 502-3. The circuit measures the difference in pressure between the activated muscle and the residual limb pressure. This principle of arranging four sensors in a bridge circuit enhances wearer control by allowing muscle activation pressures to be detected while in a seated position or standing and walking. Because the muscle activation force is large compared to normal residual limb pressure, for example as exerted by a residual limb on a surrounding socket, customizations and variations in the sensor placement may be reduced. Additionally, the system may not need to be recalibrated when the wearer dons and doffs the device.

In various embodiments, a force sensor interface component 501 is implemented in conjunction with at least one sensor component 110 wherein a Wheatstone bridge has three fixed resistors and one sensor component 110, for example, comprising a force sensing resistor or a pressure sensor. However, in various embodiments, as previously disclosed herein, a force sensor interface component 501 is implemented in conjunction with at least four sensor components 110 wherein a Wheatstone bridge has four sensor components 110, for example, each comprising a force sensing resistor or a pressure sensor. One having experience in the art will appreciate that any number of sensor components and or force sensor interface components, having any number of force sensing resistors may be implemented, to achieve various performance characteristics. For example, one force sensing interface component 501 may be implemented with four sensor components 110 comprising force sensing resistors thus providing a benefit of less calibration and fewer wires, and the system may measure the difference between the pressure on the flexed muscle inside the socket compared to the residual pressure inside the socket.

Figure 7:
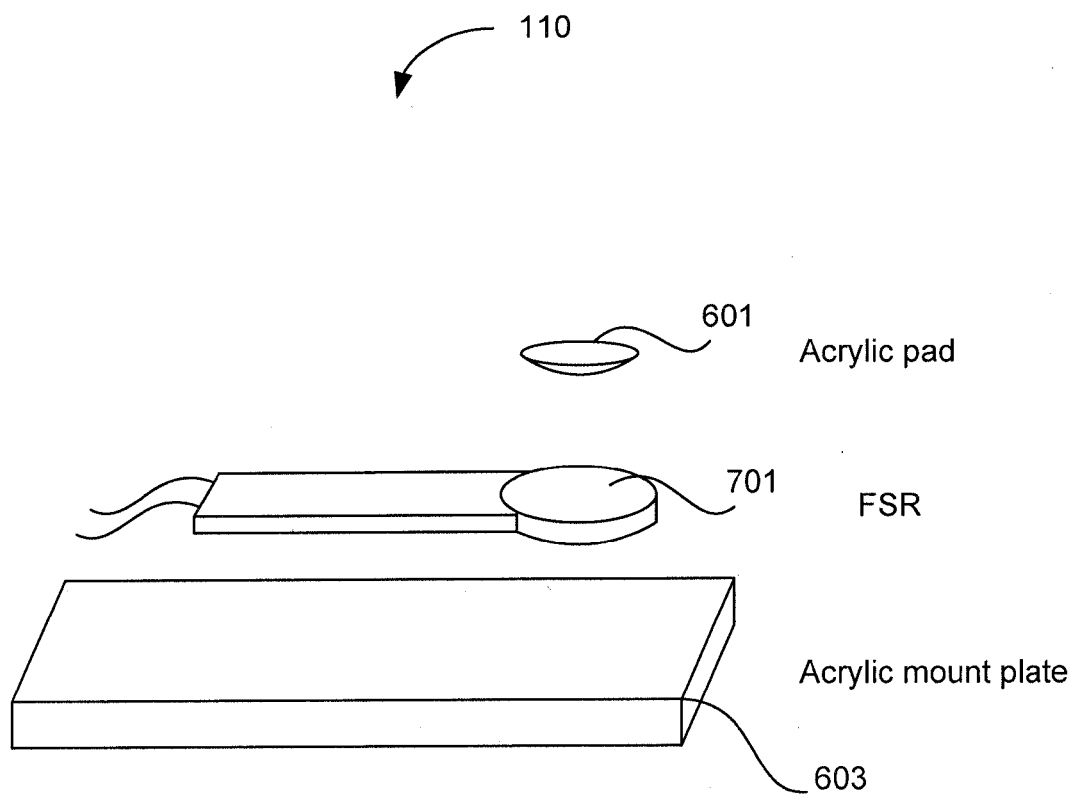
FIG. 7 illustrates various aspects of an exemplary sensor component having a force sensing resistor between a pad and a mounting plate.

In various example embodiments, a sensor component 110 comprises at least one force sensing resistor, a mounting plate, and a convex pad. For example, with reference to FIG. 7, in various embodiments a sensor component 110 comprises a force sensing resistor 701 adhered to a mounting plate 603. In various embodiments the mounting plate is acrylic, although it may be any material adapted to provide support to the force sensing resistor 701. Furthermore, the sensor component 110 may comprise a pad 601. In various embodiments, the pad is convex, although the pad may be any shape adapted to transmit pressure to the force sensing resistor 701. Still furthermore, in various embodiments, the pad comprises acrylic, although the pad may be any material adapted to provide support to the force sensing resistor 701.

In various embodiments, control component 120 comprises a first logical controller 503. Moreover, a control component 120 may comprise a logical controller comprising a dynamic pace controller. In various embodiments, a dynamic pace controller may be calibrated to provide control impulses to the actuation component 130, for example pulses corresponding to the power profile of the actuation component 130. For example, actuation component 130 may have a non-linear power-in to power-out trend. For example, the input current required to actuate the actuation component 130 may be non-linear versus the load on the actuation component 130. In various embodiments, the kinetic energy of a moving prosthesis may influence the power profile of the actuation component 130. Thus, in various embodiments, the control impulses may be adapted in correspondence to the power profile of the actuation component 130.

In various embodiments wherein prosthetic control system 100 is utilized in connection with an artificial foot and/or leg, control component 120 may comprise a logical controller utilizing tibia-based information. For example, the tibia angular velocity and the tibia angle may be sensed and a corresponding control signal may be transmitted to actuation component 130. Thus, in various embodiments, the control component 120 or the sensor component 110 may further comprise a tibia angle sensor, for example, an angular rate sensor whereby the angular velocity and the tibia angle may be evaluated.

In accordance with various embodiments, control component 120 may comprise multiple logical controllers. For example, a control component 120 may comprise a first logical controller 503 and a second logical controller 505. In various embodiments, control component 120 may comprise any number of logical controllers, for example, a first logical controller 503, a second logical controller 505, and an Nth logical controller 507. In various embodiments, a different logical controller may be activated depending on different signals received from the sensor component 110. In this manner, the wearer may change the operation of control component 120. For example, a different logical controller may be selected depending on different use profiles for prosthetic control system 100 and/or an associated prosthetic device, for example, sitting, standing, leaning, walking, running, bicycling, and driving a vehicle, among others. Moreover, control component 120 may be responsive not only to variable force imparted on sensor component 110, but control component 120 may also be responsive to sequences and patterns of muscle contraction. For example, a wearer may alternately flex and unflex a muscle to encode control messages for decoding by control component 120. In this manner, the wearer may reconfigure or change the operation of control component 120. In various embodiments, a control component 120 may have a training mode wherein the wearer can customize the behavior of the control component 120 based at least in part on the wearer's gait and preferences.

In various embodiments, control component 120 comprises a logical controller comprising pre-loaded models. For example, in a tibia based controller, a variable mathematical relation between a tibia angle (e.g., the residual limb) and the ankle angle (e.g., an angle associated with the ankle joint 132) (FIGS. 2B-C) may be modeled. Moreover, a tibia global angular position may be modeled. Moreover, a model may correspond to different points along a wearer's gait, and different models may correspond to different stride lengths. Thus, the control component 120 may select from among a plurality of pre-loaded models corresponding to the natural gait of a wearer under a plurality of conditions, for example wherein the selecting chooses a pre-loaded model corresponding to a desired gait and conditions. In various embodiments, the conditions may be derived by the controller from the input signals, or the conditions may be manually selected by the wearer, in accordance with the principles disclosed herein. In this manner, the system may approximate the natural gait of a wearer under a variety of conditions, for example so that the wearer can run or walk at various speeds and with various stride lengths.

In various embodiments, a control component 120 comprises a logical controller configured with digital filtering logic. For example, digital filtering logic may be implemented as at least one of polynomial functions, moving integral algorithms, calibration curves, and/or the like. The functions, algorithms, and/or curves may be revised over time, for example, as the prosthesis ages, or as various components change, for example, as resistors drift, or as a wearer's muscles grow or shrink. Moreover, filtering may be adjusted as the seating of a residual limb in a socket may shift during prolonged use. In this manner, control component 120 may maintain accurate control over a prosthesis, even as external and/or internal control factors vary and/or evolve.

Actuation component 130 is configured to receive signals from control component 120. Actuation component 130 may change a first characteristic of a prosthesis. In various exemplary embodiments, actuation component 130 may comprise one or more of electric motors, hydraulic actuators, pneumatic actuators, rheological fluids, variable impedance actuators, powered springs, and/or the like. Moreover, an actuation component 130 may comprise any suitable rotary and/or linear actuator, as desired. In various exemplary embodiments, an actuation component 130 may comprise a variable damping element, for example a hydraulic valve, a rheological fluid, and/or the like. An actuation component 130 may be configured to adjust one or more characteristics of a prosthetic, for example a joint position, a brace position, a joint resistance to further angular movement, and/or the like.

For example, in various embodiments, actuation component 130 comprises a robotic tendon. In various embodiments, a robotic tendon comprises a motor, a screw, and a pair of metal springs. The motor is in mechanical communication with the screw, and turns the screw when activated. In various embodiments, the screw is adapted to stretch the springs. For example, in various embodiments, the actuation component 130 may activate the motor in response to a signal from control component 120. In this manner, the motor turns the screw. The springs are stretched in response to the turning. The actuation component 130 may also reverse the direction of the motor in response to a signal from control component 120. In this manner, the springs are unstretched and/or compressed in response to the turning. By alternately stretching and unstretching/compressing the springs at different points in a wearer's stride, energy may be stored and released during a wearer's gait cycle, enabling mimicking of able-bodied walking behavior.

Additionally, the springs may lower the peak power requirement and energy consumed during the gait cycle, for example because energy is stored in the springs by the compression and expansion naturally occurring when supporting the wearer's body weight, in addition to being stored in the springs by the motor. As a result, a more efficient prosthesis may be realized.

With reference now to FIG. 1 and FIGS. 2B-2C, in an exemplary embodiment, prosthetic control system 100 is configured to adjust the position and/or angular velocity of an ankle joint 132 for a prosthetic ankle, orthosis, or brace 134. In various embodiments, with reference to FIGS. 1 and 6, a prosthetic control system 100 may be configured to adjust the position of a second prosthetic member 304 relative to a first prosthetic member 302. In various embodiments, with reference to FIGS. 1, 2B-2C, and 6, muscle activation information detected by sensor component 110 is delivered to control component 120, and control component 120 generates commands to actuation component 130. Responsive to the commands, actuation component 130 moves the ankle joint 132 and/or brace 134 and/or second prosthetic member 304. In this manner, position of a prosthetic foot may be controlled by volitional input (for example, calf muscle activation) from the wearer.

Moreover, in various embodiments, a prosthetic control system 100 may be configured to permit a wearer to position a prosthesis as desired, for example to rest a foot flat on the floor when sitting. For example, with reference to FIG. 1 and FIGS. 2A-2C, a wearer may contract a muscle 400 in proximity to a sensor component 110. Muscle 400 may exert a force on the sensor component 110, and trigger the control component 120 to direct the actuation component 130 to articulate a second prosthetic member 304 about an ankle joint 132 relative to a first prosthetic member 302. In various embodiments, the first prosthetic member 302 comprises a partial shin prosthetic and second prosthetic member 304 comprises a foot prosthetic. In this manner, the foot prosthetic may be articulated about ankle joint 132 to enable the foot to rest flat on the floor or otherwise assume a desired position and/or orientation.

It will be appreciated that, as the pressure signal from sensor component 110 is varied, the position of the ankle joint 132 may be moved. Moreover, as the pressure signal from sensor component 110 is varied, the angular velocity of the ankle joint 132 may be modified. Yet further, as the pressure signal from sensor component 110 is varied, the stiffness of the ankle joint 132 may be varied, for example via rheological fluids, springs, or variable impedance actuators. Additionally, as the pressure signal from sensor component 110 is varied, the force applied by actuation component 130 at the ankle joint 132 may be varied. Stated generally, the varying pressure signal from sensor component 110 may be utilized to vary, modify, and/or control any suitable attribute or characteristic of a prosthetic device. In this manner, improved wearer volitional control of the prosthetic device is facilitated.

Via utilization of prosthetic control system 100, a wearer can achieve control of a prosthesis, for example control of plantar flexion (downward movement) of a prosthetic foot via a powered bionic ankle. Thus, the wearer can obtain additional push-off power when walking, ascending stairs or slopes, and so forth. Additionally, the wearer can move the foot downward to push on a pedal, for example in order to control a motor vehicle.

It will be appreciated that while principles of the present disclosure may be discussed in connection with exemplary embodiments related to control of a prosthetic device, such principles may suitably be applied to braces, orthoses, exoskeletons, and/or the like. Additionally, principles of the present disclosure may be discussed in connection with exemplary embodiments related to control of the ankle joint; however, such principles may suitably be applied to the wrist, elbow, knee, hand, and so forth. All examples and embodiments provided herein are by way of illustration and not of limitation.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled", "coupling" or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A prosthetic device control system, comprising:
a prosthetic device comprising: a prosthetic ankle joint;
a first sensor set comprising:
a first sensor set comprising four sensor components arranged in a Wheatstone bridge; wherein, when the prosthetic device is coupled to a residual limb, two of the sensor components are located on top of one another and coincident with an axis of force of a muscle of the residual limb and two of the sensor components are adapted to be located coincident with an axis of force of at least one of sheer stress or normal stress between a socket of a prosthesis the prosthetic device and the residual limb, whereby common mode sensed force is filtered,
and wherein each sensor component comprises a force sensing resistor disposed within the socket of a prosthesis the prosthetic device, and wherein the sensor component is adapted to be compressed against the socket by the muscle of the residual limb;
a control component coupled to the first sensor set;

and an actuation component coupled to the control component, wherein the first sensor set receives an input from the wearer of the prosthetic device and transmits a signal to the control component, wherein the control component processes the signal received from the first sensor set, wherein the actuation component is coupled to the control component and modifies a first characteristic of the prosthetic ankle joint in response to a first instruction received from the control component, and wherein the first characteristic is selected from the group consisting of: position, velocity, force, or stiffness.

2. The system according to claim 1, wherein, when the prosthetic device is coupled to the residual limb, each sensor component is adapted to be located against the medial gastrocnemius muscle.

3. The system according to claim 1, wherein the control component comprises:
   a force sensor interface component; and
   a first logical controller, whereby the force sensor interface component electrically interfaces a sensor component and the first logical controller.

4. The system according to claim 3, wherein the force sensor interface component comprises a voltage divider.

5. The system according to claim 3, wherein the first logical controller comprises a dynamic pace controller configured to provide control impulses to the actuation component corresponding to a power profile of the actuation component having a non-linear power trend in response to a dynamic load on the actuation component.

6. The system according to claim 3, wherein the first logical controller is configured as a tibia-based controller comprising a tibia angle sensor and configured to sense a tibia angular velocity and a tibia angle and provide corresponding control impulses to the actuation component.

7. The system according to claim 3, wherein the first logical controller comprises pre-loaded models corresponding to characteristics comprising stride length and speed of a wearer under a plurality of conditions.

8. The system according to claim 3, wherein the first logical controller is configured with digital filtering logic.

9. The system according to claim 1, wherein the actuation component is selected from the group consisting of: a robotic tendon, an electric motor, a hydraulic actuator, a pneumatic actuator, or a rheological fluid actuator.

10. The system according to claim 1, further comprising a second sensor set comprising four sensors arranged at points anterior-proximal and posterior distal in the sagittal plane relative to the four sensors of the first sensor set.

* * * * *